(12) United States Patent
Park et al.

(10) Patent No.: US 11,957,432 B2
(45) Date of Patent: Apr. 16, 2024

(54) SENSING METHOD AND APPARATUS

(71) Applicant: LG INNOTEK CO., LTD., Seoul (KR)

(72) Inventors: Ju Un Park, Seoul (KR); Seong Ha Jang, Seoul (KR); Yang Hyun Joo, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 675 days.

(21) Appl. No.: 16/973,160

(22) PCT Filed: Jun. 13, 2019

(86) PCT No.: PCT/KR2019/007164
§ 371 (c)(1),
(2) Date: Dec. 8, 2020

(87) PCT Pub. No.: WO2019/240517
PCT Pub. Date: Dec. 19, 2019

(65) Prior Publication Data
US 2021/0251495 A1 Aug. 19, 2021

(30) Foreign Application Priority Data

Jun. 14, 2018 (KR) .................. 10-2018-0068364

(51) Int. Cl.
*G01S 17/894* (2020.01)
*A61B 5/00* (2006.01)
*A61B 5/02* (2006.01)
*G01S 7/4865* (2020.01)
*G06V 10/60* (2022.01)
*G06V 40/10* (2022.01)
*G06V 40/14* (2022.01)

(52) U.S. Cl.
CPC ........ *A61B 5/0059* (2013.01); *A61B 5/02007* (2013.01); *A61B 5/6887* (2013.01); *G01S 7/4865* (2013.01); *G01S 17/894* (2020.01); *G06V 10/60* (2022.01); *G06V 40/11* (2022.01); *G06V 40/14* (2022.01)

(58) Field of Classification Search
CPC ... G01S 17/894; G01S 7/4865; A61B 5/6887; A61B 5/02007
See application file for complete search history.

(56) References Cited

U.S. PATENT DOCUMENTS

2011/0150304 A1  6/2011 Abe et al.
2012/0200686 A1* 8/2012 Yu ................... A61B 1/0019
348/66

(Continued)

FOREIGN PATENT DOCUMENTS

CN 102596002 A 7/2012
CN 104856663 A 8/2015
(Continued)

*Primary Examiner* — Myron Wyche
(74) *Attorney, Agent, or Firm* — Birch, Stewart, Kolasch & Birch, LLP

(57) ABSTRACT

Disclosed are a sensing method and a sensing apparatus for acquiring information about an object according to one embodiment. In particular, disclosed are a sensing method and a sensing apparatus for obtaining the shape of blood vessels by using information regarding the intensity of received light and information regarding the distance of an object.

20 Claims, 7 Drawing Sheets

(56) References Cited

U.S. PATENT DOCUMENTS

| | | |
|---|---|---|
| 2017/0086688 A1 | 3/2017 | Masuda |
| 2019/0310490 A1* | 10/2019 | Park .................. G03B 13/32 |
| 2020/0311379 A1 | 10/2020 | Lee |

FOREIGN PATENT DOCUMENTS

| | | | | |
|---|---|---|---|---|
| JP | 2011-129004 A | | 6/2011 | |
| KR | 10-2012-0119523 A | | 10/2012 | |
| KR | 10-2014-0109158 A | | 9/2014 | |
| KR | 20140109158 | * | 9/2014 | ............ G01S 17/08 |
| KR | 10-1626837 B1 | | 6/2016 | |
| KR | 10-2017-0026125 A | | 3/2017 | |
| KR | 20170026125 | * | 3/2017 | ............... G06K 9/00 |

\* cited by examiner

[FIG. 1]
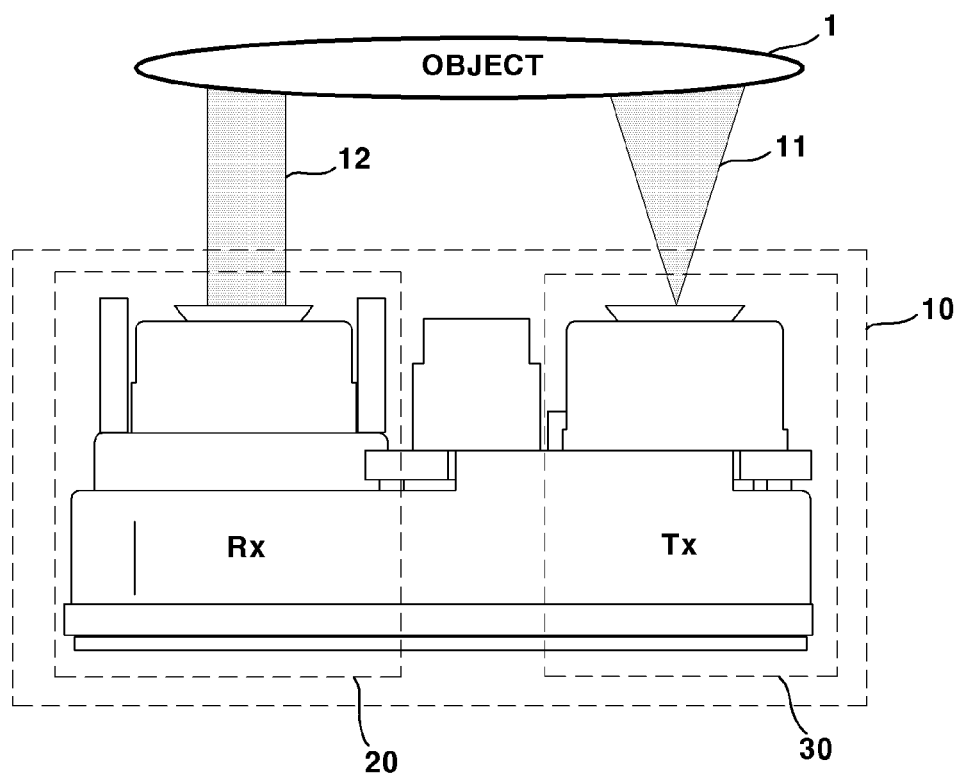

[FIG.2]
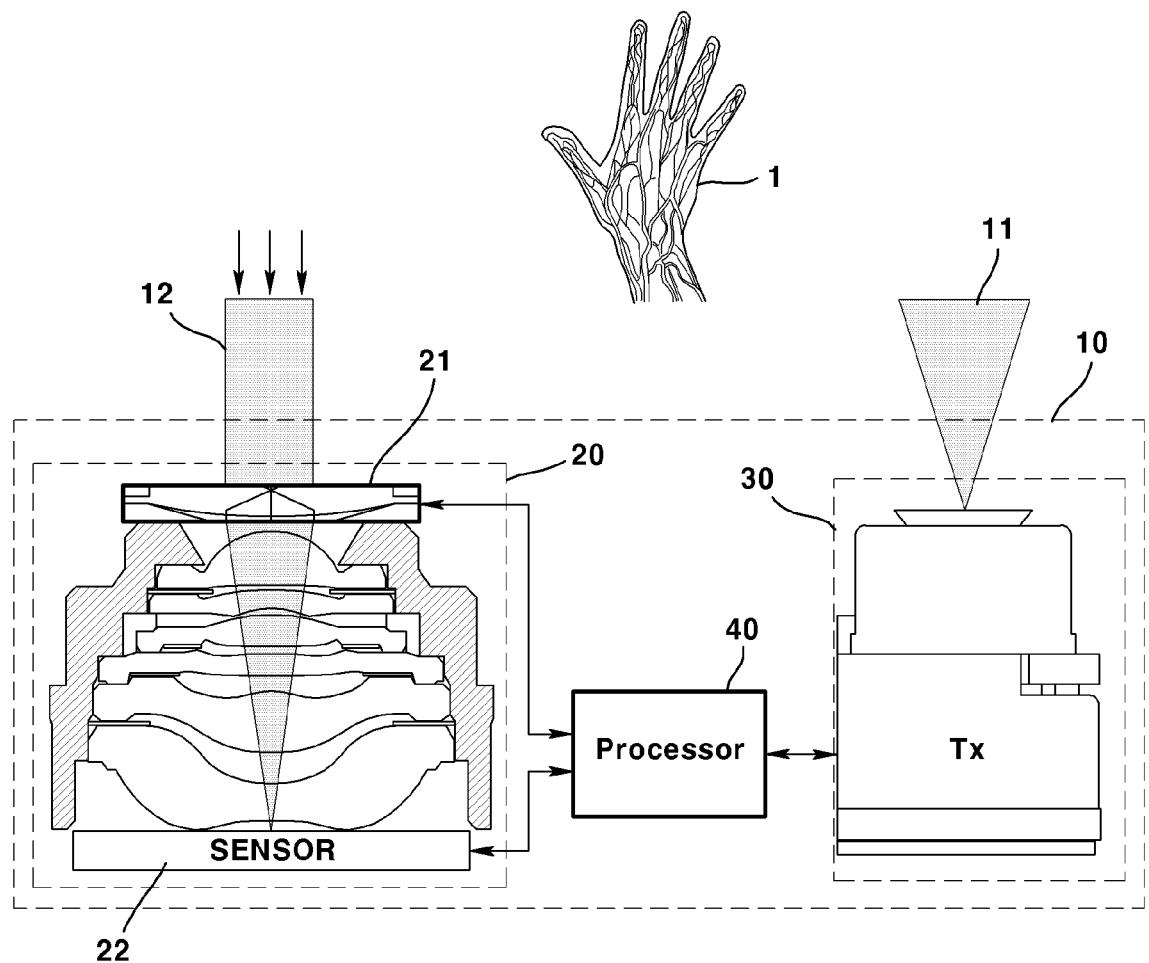

[FIG.3]
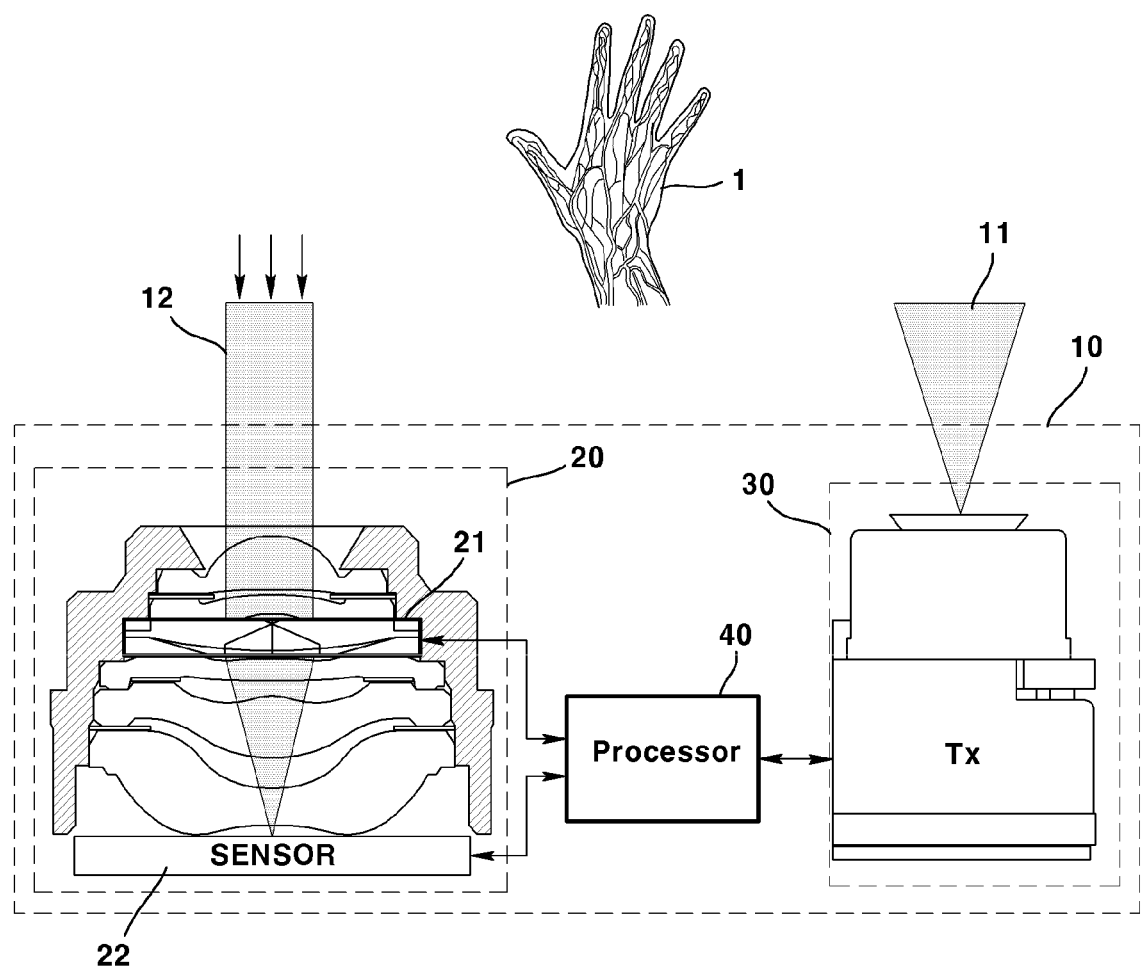

[FIG.4]
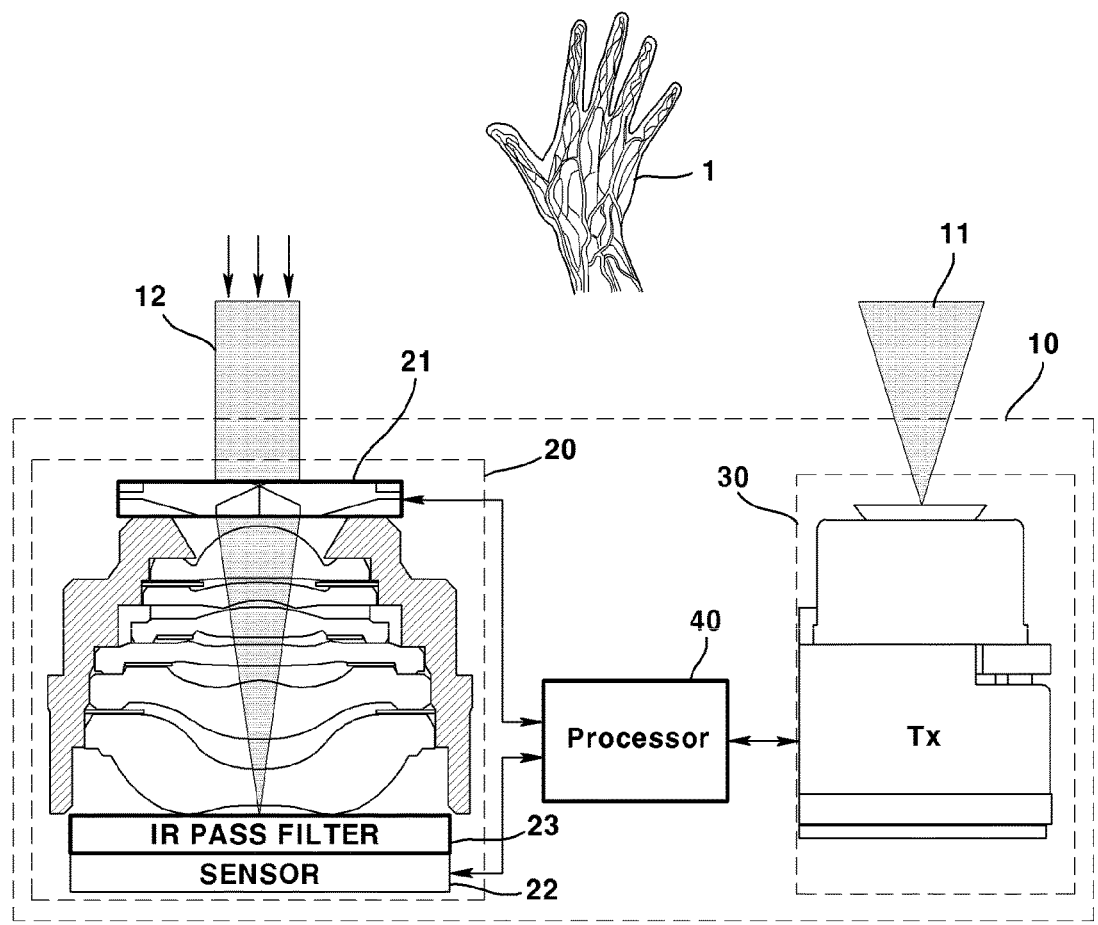

[FIG.5]
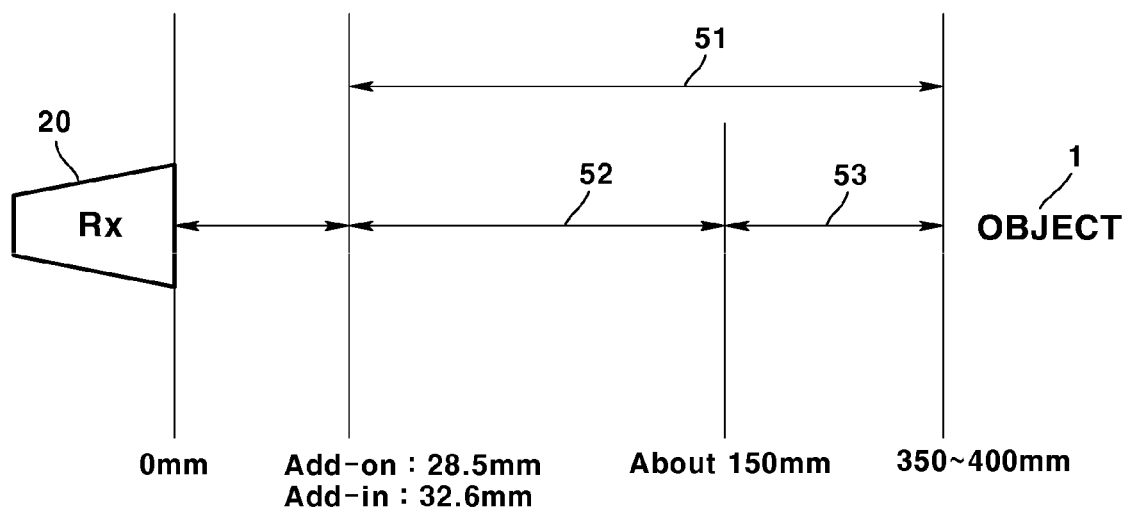

[FIG.6]
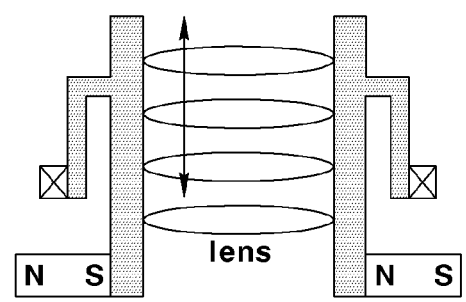

[FIG.7]
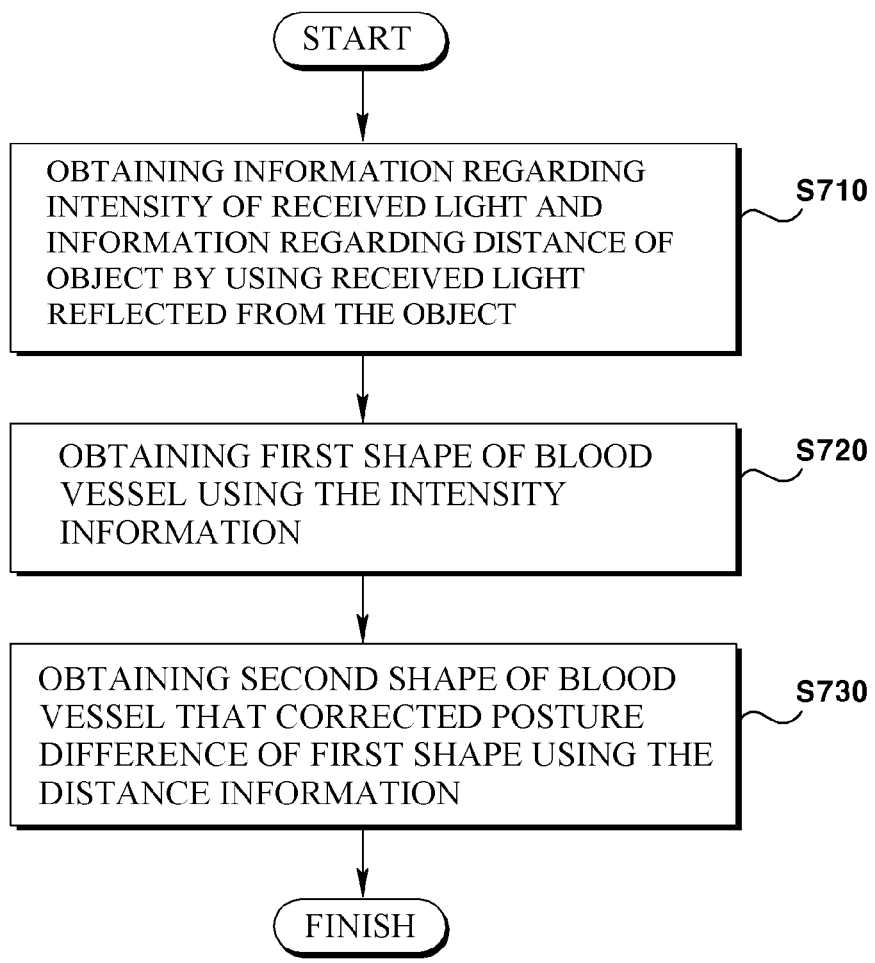

SENSING METHOD AND APPARATUS

CROSS REFERENCE TO RELATED APPLICATIONS

This application is the National Phase of PCT International Application. No. PCT/KR2019/007164, filed on Jun. 13, 2019, which claims priority under 35 U.S.C. 119(a) to Patent Application No. 10-2018-0068364, filed in the Republic of Korea on Jun. 14, 2018, all of which are hereby expressly incorporated by reference into the present application.

TECHNICAL FIELD

The present disclosure discloses a sensing method and a sensing apparatus according to one or more exemplary embodiments.

BACKGROUND OF INVENTION

Devices configured to obtain information by outputting a light and reflecting the light to an object have been used in various fields. For example, technologies from 3D (three-dimensional) cameras to distance measuring techniques configured to obtain information by outputting a light have been used by several methods.

For instance, a TOF (Time of Flight) principle is a term of a method for measuring a distance between a sensor and an object, based on the time difference between the emission of a signal and its return to the sensor, after being reflected by an object. The ToF technique is used in a variety of fields including aviation, shipbuilding, civil engineering, camera and survey because it implementation method is simple.

DETAILED DESCRIPTION OF INVENTION

Technical Subject

The present disclosure discloses a sensing method configured to obtain information on an object by sensing a light and a sensing apparatus thereof according to one or more exemplary embodiments. To be more specific, disclosed are a method and apparatus configured to obtain information on an object through light intensity information or object distance information.

The technical subjects to be solved are not limited to those mentioned above, and may further include various technical subjects within a scope apparent to those skilled in the art.

Technical Solution

In one general aspect of the present disclosure, there may be provided a sensing apparatus comprising:
- a sensor for obtaining intensity information of a received light and distance information of an object using the received light reflected from the object; and
- a processor for obtaining a first shape of blood vessel of the object using the intensity information and obtaining a second shape of the blood vessel using the distance information and the first shape of the blood vessel.

Furthermore, the first shape and/or the second shape may include thickness information of the blood vessel.

Furthermore, the apparatus may include a liquid lens for controlling a focus of the received light.

Furthermore, the second shape may be a shape reflected by posture difference information of the first shape.

Furthermore, the first shape may be determined based on a region where intensity of the received light is relatively weak.

Furthermore, the processor may compare the second shape with a standard shape stored in a storage.

Furthermore, the apparatus may increase an angle of view by controlling the liquid lens when a distance from the sensor to the object is smaller than a pre-set value.

In a second general aspect of the present disclosure, there may be provided a camera module comprising:
- a light source for outputting an infrared light to an object;
- a liquid lens for controlling a focus of a received light reflected from the object;
- a sensor for obtaining intensity information of the received light and distance information of the object; and
- a processor for obtaining a first shape of blood vessel of the object using the intensity information and obtaining a second shape of the blood vessel using the distance information and the first shape of the blood vessel.

Furthermore, the processor may decrease the power of the infrared light outputted from the light source when the power of the received light received from the sensor is saturated.

Furthermore, the processor may decrease an amount of light output per time of the light source or decrease the exposure time relative to the received light of the sensor when the power of the received light received from the sensor is saturated.

Furthermore, the processor may increase an angle of view by controlling the liquid lens when a distance from the sensor to the object is smaller than a pre-set value.

Furthermore, the distance information may include information showing a distance from the sensor to the object, and the liquid lens may perform an autofocusing in response to the distance information.

In a third general aspect of the present disclosure, there may be provided a sensing method comprising:
- obtaining intensity information of a received light and distance information of an object using the received light reflected from the object; and
- obtaining a first shape of blood vessel of the object using the intensity information and obtaining a second shape of the blood vessel corrected in posture difference of the first shape of the blood vessel using the distance information.

In a fourth general aspect of the present disclosure, there may be provided a sensing method comprising:
- outputting an output light to an object;
- obtaining intensity information of received light obtained by allowing the output light to be reflected from the object and obtaining distance information of the object;
- obtaining a shape of blood vessel of the object and thickness information using the intensity information; and
- obtaining 3D information of the blood vessel using the shape of the blood vessel, thickness information and the distance information.

In a fifth general aspect of the present disclosure, there may be provided a recording medium for reading the methods of the third aspect and the fourth aspect using a computer recorded with a program for executing in a computer.

Advantageous Effects of Invention

The present disclosure discloses a sensing method configured to obtain information on an object by sensing a light and a sensing apparatus thereof according to one or more exemplary embodiments.

BRIEF DESCRIPTION OF DRAWINGS

FIG. 1 is a conceptual diagram illustrating an operation of a sensing apparatus according to an exemplary embodiment of the present disclosure.

FIG. 2 is a conceptual diagram illustrating an operation of a sensing apparatus by being interacted with a light source according to an exemplary embodiment of the present disclosure.

FIG. 3 is a conceptual diagram illustrating an operation of a sensing apparatus included therein with a lens by being interacted with a light source according to an exemplary embodiment of the present disclosure.

FIG. 4 is a conceptual diagram illustrating a case where a sensing apparatus includes an IR pass filter.

FIG. 5 is a schematic view illustrating an exemplary embodiment where a sensing apparatus is operated in response to a distance between a sensor and an object.

FIG. 6 is a schematic view illustrating an example of a solid lens included in a sensing apparatus according to an exemplary embodiment of the present disclosure.

FIG. 7 is a flowchart illustrating a method for obtaining, by a sensing apparatus, a second shape according to an exemplary embodiment of the present disclosure.

BEST MODE

The terms used in the exemplary embodiments were selected from widely used general terms, wherever possible, in consideration of functions of the present disclosure, which, however, may be changed depending on intention of those skilled in the art, judicial precedents or appearance of new technologies. Furthermore, in particular cases, there may be terms arbitrarily selected by the applicant, and in this case, detailed meanings thereof will be described at the description of the relevant invention. Therefore, the terms used in the present disclosure are not names of simple terms but may be defined based on meaning of the terms and contents throughout the present disclosure.

Throughout the specification, unless explicitly described to the contrary, the word "comprise", "include" and variations such as "comprises", "comprising", "includes" and "including" will be understood to imply the inclusion of stated elements but not the exclusion of any other element. The terms "comprises," and/or "comprising" are inclusive and therefore specify the presence of stated elements, steps and/or operations, but do not preclude the presence or addition of one or more other elements, steps and/or operations thereof.

Furthermore, the terms "part" and "module" described in the specification may mean units for processing at least one function and operation and can be implemented by hardware components or software components, and combinations thereof.

With reference to the following drawings, exemplary embodiments of the present disclosure will be described in detail to allow being easily implemented by the skilled in the art belonging to the present disclosure. However, this disclosure may be embodied in many different forms and should not be construed as limited to the embodiments set forth herein.

Hereinafter, exemplary embodiments of the present disclosure will be described in detail with reference to the accompanying drawings.

FIG. 1 is a conceptual diagram illustrating an operation of a sensing apparatus (20) according to an exemplary embodiment of the present disclosure.

As shown in FIG. 1, the sensing apparatus (20) may operate together with the light source (30). Furthermore, the sensing apparatus (20) and the light source (30) may be included in a camera module (10).

Referring to FIG. 1, the sensing apparatus (20) may obtain a received light (12) of an output light (11) outputted from the light source (30) that is reflected from an object (1).

The sensing apparatus (20) according to an exemplary embodiment of the present disclosure may obtain intensity information of the received light (12) and distance information of the object (1) from the received light (12).

The intensity information of the received light (12) may include an intensity value of the received light (12) based on a region. Furthermore, the distance information of the object (1) may show a distance between the sensing apparatus (20) and the object (1).

The detailed configuration of sensing apparatus (20) and operation thereof will be further explained in detail in FIG. 2 and subsequent drawings thereof.

FIG. 2 is a conceptual diagram illustrating an operation of a sensing apparatus (20) by being interacted with a light source (30) according to an exemplary embodiment of the present disclosure.

Referring to FIG. 2, the sensing apparatus (20) may include a sensor (22) and a lens (21). However, it should be apparent to those skilled in the art that other general-purpose elements may be further included in the sensing apparatus (20) in addition to the elements illustrated in FIG. 2. For example, the sensing apparatus (20) may further include a processor (40). In another example, the sensing apparatus (20) may further include a memory not shown) connected to the processor (40). Alternatively, in still another exemplary embodiment, it should be apparent to those skilled in the art that some elements among the elements illustrated in FIG. 2 may be omitted.

The sensing apparatus (20) according to an exemplary embodiment of the present disclosure may be disposed with a sensor (22) and a processor (40).

The light source (30) according to an exemplary embodiment of the present disclosure may output an output light (11). The output light (11) is a light outputted from the light source (30), and may be a wavelength within a pre-set scope.

The light source (30), for example, may be an LED (Light Emitting Diode) capable of emitting a light with infrared wavelength and emitting a light having invisible near-infrared wavelength of about 850 nm, an LD (Laser Diode) or a VCSEL (Vertical-Cavity Surface-Emitting Laser), but bandwidth of wavelength and types of light source may not be limited thereto. For example, wavelength of output light outputted from the light source (30) may include a visible light region and may also include a ultraviolet region.

According to an exemplary embodiment, the output light (11) outputted from the light source (30) may be infrared light. Although the following exemplary embodiments explain a case where the output light (11) is infrared light, the embodiments should not be restrictively interpreted to a case of infrared light. Not only a case of the output light (11)

being of infrared light, but also UV (Ultraviolet ray), visible light and x rays may be included in the right scope of the present disclosure.

In response to a control signal received from the processor (40), the light source (30) may output an output light (11) by performing an amplitude modification or phase modification, for example. In response to the control signal of the processor (40), the output light (11) outputted from the light source (30) to the object (1) may take a shape of a periodic continuous function having a predetermined period. For example, the output light (11) may have a particularly defined waveform such as a sine wave, a lamp wave, a square wave and a pulse wave, but the output light (11) may have s non-defined generally shaped waveform.

The sensor (22) according to an exemplary embodiment may obtain intensity information of the received light (12) and distance information of object (1) using the received light (12) reflected from the object (1). The sensor (22) may distinguish an output light (11) outputted from the light source (30) among various lights introduced into the sensor (22) from a received light (12) obtained by being reflected from the object (1). For example, when the light source (30) output an output light in the range of 750 nm-950 nm, the sensor (22) may selectively obtain a light in the range of 750 nm-950 nm through filtering. Furthermore, the sensor (22) may obtain accurate information on the object (1) by selectively obtaining a received light corresponding to an output light.

The sensor (22) may obtain intensity information of the received light (12) reflected from the object (1). In case the output light (11) is an infrared light, the sensor (22) may distinguish a sensed region of the object (1) according to infrared absorption degree. For example, when the object (1) includes a first region and a second region, where the first region has a high infrared absorption rate while the second region has a low infrared absorption rate, the sensor (22) may distinguish the first region from the second region using the intensity information of received light (12). To be more specific, when the intensity of received light (12) is lower than a pre-set value in the first region and the intensity of received light (12) is greater than a pre-set value in the second region, the sensor (22) may distinguish the first region from the second region through the intensity information of the received light (12).

According to an exemplary embodiment, when an object (1) is a part of a human body, a sensed region of the object (1) may be classified to a plurality of regions in response to characteristics of hemoglobin. To be more specific, the characteristics of hemoglobin absorbing the infrared light may be used. For example, in case the output light (11) is an infrared light, the sensor (22) may determine a region of intensity of received light (12) being relatively great as a region of no blood vessel, based on the intensity information of received light (12), and may determine a region of relatively small in the intensity of received light (12) as a region of blood vessel.

According to an exemplary embodiment, the meaning that intensity of received light (12) is relatively great may mean that the intensity of received light (12) is greater than an average value of entire region, and the meaning that intensity of received light (12) is relatively small may mean that the intensity of received light (12) is smaller than an average value of entire region. Furthermore, a region having a relatively great intensity in the received light (12) may mean a region having a greater intensity in the received light (12) than a pre-set value, and a region having a relatively small intensity in the received light (12) may mean a region having a smaller intensity in the received light (12) than a pre-set value. In this case, the pre-set value may be determined by intensity of output light (11).

The sensor (22) may obtain distance information of object (1) using the received light (12) reflected from the object (1). The distance information may exhibit a distance from a pre-set position to an object (1). For example, the distanced information may include information on a distance from a camera module (10) to an object (1), a distance from a light source (30) to an object (1), a distance from a sensor (22) to an object (1) and a distance from a sensing apparatus (20) to an object (1).

As explained in the following description, the sensor (22) according to an exemplary embodiment may obtain distance information in the manner of TOF (Time-of-Flight) method.

The sensor (22) according to an exemplary embodiment may obtain distance information using a time difference between a standard time of output light (11) emission and an obtainment time of received light (11) returned by allowing the output light (11) to be reflected from the object (1).

The sensor (22) according to an exemplary embodiment may obtain distance information using a difference between a first phase of the output light (11) outputted from the light source (30) and a second phase of received light (12) returned by allowing the output light (11) to be reflected from the object (1). When a distance is determined using a phase difference, a periodic wave may be used as an output light (11).

The processor (40) according to an exemplary embodiment may calculate distance information in response to distance information obtainment algorithm. The distance information obtainment algorithm may be pre-set. The processor (40) may be embodied by a dedicated IC, or alternatively, may be embodied by software installed inside the camera module (10). In case of being embodied by software, the distance information obtainment algorithm may be stored in a memory included in the camera module (10).

The processor (40) according to an exemplary embodiment may obtain a first shape of blood vessel of object (1) using intensity information.

The first shape according to an exemplary embodiment may be obtained through the intensity information of received light (12). For example, the first shape may be a shape shown by a region where intensity of received light (12) in the sensed region is less than a first value. In another example, the first shape may be a shape shown by a region where intensity of received light (12) in the sensed region is less than a first value and may be a shape by a region where intensity of received light (12) in the sensed region is greater than a second value. In still another example, the first shape may be a shape shown by a region where intensity of received light (12) in the sensed region is greater than a third value.

In case the output light (11) is an infrared light, and because hemoglobin included in blood vessel absorbs the infrared light, a region corresponding to the blood vessel in the sensed region may have the intensity of received light (12) less than a pre-set value. As a result, the processor (40) may obtain a first shape which is a shape shown by a region less than a first value in the intensity of received light (12) in the sensed region. Furthermore, the processor (40) may use one or more algorithms pre-set in the course of obtaining the first shape.

The processor (40) according to an exemplary embodiment may obtain a first shape by reflecting the characteristics that blood vessels are mutually interconnected. For example, the first shape may be determined by mutually connecting regions where intensity of received light (12) is less than a first value, and mutually connecting regions recognized as having a thickness less than a pre-set value.

The processor (40) according to an exemplary embodiment may obtain a first shape by reflecting the characteristics that blood vessels are encompassed by the human body. For example, the processor (40) may separate an empty space (void) from a part recognized by the human body, and may determine, as a first shape, an area shown by a region where the intensity of received light (12) in a region recognized as human body is less than a first value.

The processor (40) according to an exemplary embodiment may obtain an image for obtaining a first shape using the intensity information. The image for obtaining the first shape may be an image included by the intensity information of received light (12). For example, the image for obtaining the first shape may be an image shown by contrast in the intensity information of received light (12).

The processor (40) according to an exemplary embodiment may obtain a first shape of blood vessel of object (1) by using the intensity information. In case an object (1) is a hand according to an exemplary embodiment, the processor (40) may obtain a first shape, which is a shape of blood vessel included in the hand, and which is in turn the object (1), using the intensity information. For example, the first shape may be a 2D (two-dimensional) image shape illustrated by a region where intensity of infrared light is less than a pre-set value.

The first shape according to an exemplary embodiment may include thickness information of blood vessel. To be more specific, the processor (40) may obtain the thickness information of blood vessel using the intensity information of received light (12). The processor (40) according to an exemplary embodiment may determine a blood thickness through a pre-set algorithm. For example, thickness of blood vessel may be determined by modeling a blood in a particular shape (e.g., cylindrical shape) in response to thickness of blood vessel in one aspect determined through intensity thickness of received light (12).

The processor (40) according to an exemplary embodiment may obtain a second shape of blood vessel using the distance information and the first shape.

The processor (40) according to an exemplary embodiment may obtain distance information of object (1). For example, the processor (40) according to an exemplary embodiment may obtain distance information on each pixel included in the sensed region. The processor (40) according to an exemplary embodiment may obtain information on the shape, appearance and the like of object (1).

Furthermore, the processor (40) may do the modelling of a basic shape of an object (1) by comparing the sensed shape of object (1) with a pre-set shape. For example, when an object (1) is a hand, and an index finger and a thumb are mutually attached, a shape of the index finger and the thumb being separated may be modelled.

However, because the distance information obtains an outer appearance of an object (1), information on blood vessel may not be directly contained in the distance information. Therefore, the processor (40) may obtain a second shape of blood vessel using a first shape and distance information together.

Hereinafter, although the following description focuses on a case where an object (1) is a hand, the present disclosure is not limited thereto.

The first shape may show a shape of blood vessel corresponding to a current hand shape. Furthermore, the processor (40) may determine a current hand shape through distance information. Thus, a 3D shape of blood vessel corresponding to a current hand shape may be determined by combining a 2D or a 3D shape of blood vessel and a 3D shape of hand. In this case, the second shape of blood shape may be a 3D shape.

Furthermore, the determined 3D shape of blood vessel may be modelled to correspond to a pre-set hand shape. For example, when a 3D shape of blood vessel is obtained while a hand is tilted at a 15° by combining a 2D shape of blood vessel and a 3D shape of a hand, a 3D shape of blood vessel can be modelled that is laid on a plain surface while a hand is not tilted through a pre-set algorithm based on the obtained 3D shape of blood vessel. In this case, the finally obtained second shape of blood vessel may be a 2D shape. Thus, the processor (40) may obtain a shape of blood vessel on a standard shape (e.g., a shape of all fingers being unfolded on a plain surface) through the modelling regardless of a current hand shape.

The second shape according to an exemplary embodiment may include thickness information of blood vessel. To be more specific, the processor (40 may obtain the thickness information of blood vessel using distance information and a first shape. The processor (40) according to an exemplary embodiment may determine the thickness of blood vessel through the pre-set algorithm. For example, the thickness of blood vessel may be determined by modelling the blood vessel in a particular shape (e.g., cylindrical shape based on the distance information and information obtained from the first shape. The processor (40) may obtain thickness information of blood vessel by modelling a blood vessel in a 3D method.

The second shape may be reflected by posture difference information of first shape. The second shape may take a shape reflected by the posture difference information because of being obtained through distance information. To be more specific, both the information obtained through the first shape and the posture difference information obtained through distance information may be all reflected on the second shape.

A lens (21) according to an exemplary embodiment may include a liquid lens or a solid lens. The lens (21) may control a focus of received light (12). The method of controlling the focus of lens (21) may be pre-set depending on types of lenses (21).

The liquid lens may include liquid, plate and electrodes. The liquid may include a conductive liquid and a non-conductive liquid, and the electrodes may be disposed on or under the plate. Furthermore, the electrode may include a common terminal and a plurality of individual terminals. One common terminal may be disposed and the individual terminal may be in the plural number. The plate may include a first plate including a cavity disposed with liquid, and may further include a second plate on or under the first plate. Furthermore, the liquid lens may further include a third plate to allow the first plate to be disposed between the second plate and the third plate. A focal distance may be changed by allowing a shape of interface formed with the conductive liquid and the non-conductive liquid to be changed in response to a driving voltage applied between the common terminal and the individual terminal. The processor (40) may supply a driving voltage to the liquid lens and may be disposed on a sensor substrate disposed with an image sensor.

Now, referring to FIG. 2, the lens (21) may be disposed with an add-on type. The add-on type means a structural type disposed with a liquid lens on solid lenses. However, the present disclosure is not limited thereto, and the lens (21), as illustrated in FIG. 3, may be also disposed with an add-in type. The add-in type means a type disposed with a liquid lens among solid lenses.

The processor (40) according to an exemplary embodiment may compare a second shape with a standard shape stored in the storage. The second shape may take a shape modelled after a shape corresponding to the standard shape. For example, in a case where an object (1) is a hand, the second shape may be compared with the standard shape by being modelled after a shape where all fingers are unfolded on a plain surface. Furthermore, the processor (40) may perform a certification based on a comparison result. To be more specific, the processor (40) may perform the certification by comparing a shape of blood vessel (e.g., vein) of object (1) with a shape stored in the storage.

The processor (40) according to an exemplary embodiment may unlock a locked state when a shape of blood vessel (e.g., vein) of object (1) corresponds to a shape pre-stored in the storage.

The processor (40) according to an exemplary embodiment may reduce the power of infrared light by controlling a light source (30) emitting an infrared light when a power of received light (12) is saturated. Alternatively, the processor (40) according to an exemplary embodiment may reduce a received amount of received light (12) per hour when the power of received light (12) is saturated, or reduce an exposed time relative to the received light (12) of sensor (22). The processor (40) may control the light source (30) or the sensor (22) lest the power of received light (12) be saturated when the power of received light (12) is saturated.

In case the camera module (10) is disposed with an aperture or a shutter, the processor (40), when the power of received light (12) is saturated, may control the aperture or the shutter to decrease the received amount of received light (12) per hour or reduce an exposed time relative to the received light (12) of sensor (22).

The processor (40) according to an exemplary embodiment may increase an angle of view by controlling a lens (21, e.g., liquid lens) when a distance from the sensor (22) to an object (1) is less than a pre-set value.

The distance information according to an exemplary embodiment may include information showing a distance from the sensor (22) to the object (1), and the lens (21, e.g., liquid lens) may perform an autofocusing based on the distance information.

Now, operations of camera module will be described based on order.

The light source (30) may output an output light (11) to an object (1) in a first step. The sensing apparatus (20) according to an exemplary embodiment may obtain intensity information of received light (12) obtained by allowing the output light (11) to be reflected from the object (1) and distance information to the object (1) in a second step. The sensing apparatus (20) according to an exemplary embodiment may obtain a shape of blood vessel of the object (1) and thickness information using intensity information in a third step. For example, the sensing apparatus (20) may obtain a 3D shape of blood vessel using the intensity information. In this case, the sensing apparatus (20) may obtain a 3D shape of blood vessel using a pre-set algorithm and intensity information.

In a fourth step, the sensing apparatus (20) according to an exemplary embodiment may obtain a shape of object (1) using the distance information. For example, the sensing apparatus (20) may determine a hand shape or a hand appearance.

In a fifth step, the sensing apparatus (20) according to an exemplary embodiment may obtain a shape of blood vessel in response to the shape of object (1) using the shape and thickness information of blood vessel and the shape of object (1). The sensing apparatus (20) may determine a shape of blood vessel corresponding to a current hand shape. The shape of blood vessel may be a shape corresponding to a current hand shape, or a shape so modeled as to correspond to the standard shape.

FIG. 3 is a conceptual diagram illustrating an operation of a sensing apparatus (20) included therein with a lens (31) by being interacted with a light source (30) according to an exemplary embodiment of the present disclosure.

Referring FIG. 3, the lens (21) may be disposed with an add-in type. To be more specific, the lens (21) may be included within the sensing apparatus (20). The lens (21) may operate by being interacted with other lenses included in the sensing apparatus (20), and may control a focus relative to the sensor of received light (12).

FIG. 4 is a conceptual diagram illustrating a case where a sensing apparatus (20) includes an IR pass filter (23).

The light source (30) according to an exemplary embodiment may output an output light (11). The output light (11) may be a light outputted from the light source (30), and may be a wavelength within a pre-set range.

The light source (30) may output a light having an infrared wavelength, and FIG. 4 will disclose an exemplary embodiment of a case where the light source (30) outputs an infrared light.

The sensor (22) may selectively obtain a received light obtained by allowing an output light (11) emitted from the light source (30) among several lights introduced into the sensor (22) to be reflected from the object (1). For example, in a case when the light source (30) outputs an output light in the range of 750 nm-950 nm, the sensor (22) may selectively obtain a light in the range of 750 nm-950 nm through filtering. Furthermore, the sensor (22) may obtain an accurate information on the object (1) by selectively obtaining the received light corresponding to the output light, and a filter may be used in the said process. For example, when the output light (11) outputted from the light source (30) according to an exemplary embodiment is an infrared light, an IR (Infrared) pass filter is disposed on the sensor (22) whereby the sensor (22) can selectively obtain the infrared light, as illustrated in FIG. 4.

FIG. 5 is a schematic view illustrating an exemplary embodiment where a sensing apparatus (20) is operated in response to a distance between a sensor (22) and an object (1).

The sensing apparatus (20) according to an exemplary embodiment may operate when a distance between the sensor (22) and the object (1) is within a range of a third distance (51).

When a distance between the sensor (22) and the object (1) is changed from a first distance (53) to a second distance (52) according to an exemplary embodiment, the sensing apparatus (20) may decrease an ROC (Radius of Curvature) of liquid lens contained in the sensing apparatus (20). To be more specific, when a distance between the sensor (22) and the object (1) is decreased, the processor (40) may increase a curvature of liquid lens by controlling the liquid lens so that a radius value corresponding to the liquid lens can be decreased.

When a distance between the sensor (22) and the object (1) is changed from a second distance (52) to a first distance (53) according to an exemplary embodiment, the sensing apparatus (20) may increase an ROC (Radius of Curvature)

of liquid lens contained in the sensing apparatus (20). To be more specific, when a distance between the sensor (22) and the object (1) is increased, the processor (40) may decrease a curvature of interface of liquid lens by controlling the liquid lens so that a radius value corresponding to the liquid lens can be increased.

The processor (40) according to an exemplary embodiment may control a current or a voltage applied to a liquid lens in order to control the ROC of the liquid lens. The detailed method for controlling the current or voltage applied to the liquid lens in order to control the ROC of the liquid lens may be determined by the characteristics of liquid lens (e.g., specification, circuit characteristics, etc.).

FIG. 6 is a schematic view illustrating an example of a solid lens included in a sensing apparatus (20) according to an exemplary embodiment of the present disclosure.

The lens (21) contained in the sensing apparatus (20) according to an exemplary embodiment may be a solid lens. The sensing apparatus (20) may control a focus of the received light (12) using the solid lens. To be more specific, the focus of received lens (12) may be controlled by allowing the solid lens to be vertically moved, as illustrated in FIG. 6. A magnetic force may be used in order to control a position of solid lens.

FIG. 7 is a flowchart illustrating a method for obtaining, by a sensing apparatus (20), a second shape according to an exemplary embodiment of the present disclosure.

The detailed operational method of the sensing apparatus (20) may be referenced to the contents disclosed in FIG. 2.

The sensing apparatus (20) according to an exemplary embodiment may obtain intensity information of received light (12) and distance information of object (1) using the received light (12) reflected from the object (1) (Step S710).

The sensing apparatus (20) may selectively obtain the received light (12) obtained by allowing the output light (11) outputted from the light source (3) among several lights introduced into the sensing apparatus (20) to be reflected from the object (1). The sensing apparatus (20) may obtain not only the intensity information of received light (12) but also the distance information showing a distance between the sensing apparatus (20) and the object (1) through the sensor (22) included in the sensing apparatus (20).

The sensing apparatus (20) according to an exemplary embodiment may obtain a first shape of blood vessel of object (1) using the intensity information (Step S720).

The first shape according to an exemplary embodiment may be obtained through the intensity information of the received light (12). For example, the first shape may be a shape shown by a region where intensity of received light (12) in a sensed area is less than a pre-set value, but the present disclosure is not limited thereto.

The sensing apparatus (20) according to an exemplary embodiment may obtain a second shape of blood vessel where a posture difference of the first shape of blood vessel is corrected using the distance information (Step S730).

The first shape may be a shape determined by posture of a current object (1). The sensing apparatus (20) may determine a current shape or posture of object (1) using the distance information, and obtain the second shape by correcting the posture difference. For example, the second shape may show a shape of blood vessel on a standard shape (e.g., a shape of all fingers being unfolded on a plain surface) by allowing the posture difference to be corrected.

Meantime, the aforesaid methods may be written by a program executed by a computer, and may be implemented by a general-purpose digital computer capable of operating the said program using a recording medium readable by a computer. Furthermore, data structures used in the aforementioned methods may be recorded on recording media readable by a computer through various means. The computer-readable media may comprise storage media such as magnetic storage devices (e.g., RAM, ROM, USB, floppy disk, hard disk, etc.) and optical reading media (e.g., CD-ROM, DVD). It should be understood that numerous other modifications can be devised by those skilled in the art that will not deviate from the aforementioned essential characteristics of the technical fields related to the principles of this disclosure. Therefore, it should be understood that the above-described embodiments are not limited by any of the details of the foregoing description and drawings, but defined by appended claims, and it should be interpreted that all the differences within the equivalent scopes thereof are included in the present disclosure.

The invention claimed is:

1. A sensing apparatus comprising:
a sensor obtaining an intensity information of a received light and a distance information of an object using the received light reflected from the object; and
a processor obtaining a first shape of a blood vessel of the object using the intensity information and obtaining a second shape of the blood vessel using the distance information and the first shape of the blood vessel,
wherein the processor obtains a shape of the object using the distance information, performs modelling of a basic shape of the object by comparing the obtained shape of the object with a pre-set shape, and determines the second shape of the blood vessel by combining the basic shape of the object and the first shape of the blood vessel, and
wherein the second shape is a shape reflected by a posture difference information of the first shape.

2. The sensing apparatus of claim 1, wherein the first shape or the second shape includes a thickness information of the blood vessel.

3. The sensing apparatus of claim 1, comprising a liquid lens controlling a focus of the received light.

4. The sensing apparatus of claim 1, wherein the second shape is a shape of a blood vessel in a shape of all fingers unfolded on a plane surface.

5. The sensing apparatus of claim 1, wherein the first shape is determined based on a region where intensity of the received light is relatively weak.

6. The sensing apparatus of claim 1, wherein the first shape is determined based on a region where intensity of the received light is smaller than an average value of entire region or a pre-set value.

7. The sensing apparatus of claim 1, wherein the processor compares the second shape with a standard shape stored in a storage.

8. The sensing apparatus of claim 3, configured to increase an angle of view by controlling the liquid lens when a distance from the sensor to the object is smaller than a pre-set value.

9. The sensing apparatus of claim 3, wherein the liquid lens is an add on type or an add in type.

10. The sensing apparatus of claim 1, wherein the processor decreases a receiving amount per hour of the received light or an exposed time of the received light of the sensor when a power of the received light received from the sensor is saturated.

11. A camera module comprising:
a light source outputting an infrared light to an object;
a liquid lens controlling a focus of a received light reflected from the object;

a sensor obtaining an intensity information of the received light and a distance information of the object; and a processor obtaining a first shape of a blood vessel of the object using the intensity information and obtaining a second shape of the blood vessel using the distance information and the first shape of the blood vessel, wherein the processor obtains a shape of the object using the distance information, performs modelling of a basic shape of the object by comparing the obtained shape of the object with a pre-set shape, and determines the second shape of the blood vessel by combining the basic shape of the object and the first shape of the blood vessel, and wherein the second shape is a shape reflected by a posture difference information of the first shape.

12. The camera module of claim 11, wherein the processor decreases a power of the infrared light outputted from the light source when a power of the received light received from the sensor is saturated.

13. The camera module of claim 11, wherein the processor decreases an amount of light output per time of the light source or an exposure time of the received light of the sensor when the power of the received light received from the sensor is saturated.

14. The camera module of claim 11, wherein the processor increases an angle of view by controlling the liquid lens when a distance from the sensor to the object is smaller than a pre-set value.

15. The camera module of claim 11, the distance information includes an information representing a distance from the sensor to the object, and the liquid lens performs an autofocusing in response to the distance information.

16. The camera module of claim 11, wherein the first shape is determined based on a region where intensity of the received light is relatively weak.

17. The camera module of claim 11, wherein the first shape is determined based on a region where intensity of the received light is smaller than an average value of entire region or a pre-set value.

18. The camera module of claim 11, wherein the second shape is a shape of a blood vessel in a shape of all fingers unfolded on a plane surface.

19. The camera module of claim 11, wherein the processor compares the second shape with a standard shape stored in a storage.

20. A sensing method comprising:

outputting an output light to an object;

obtaining an intensity information of a received light obtained by allowing the output light to be reflected from the object and obtaining a distance information of the object;

obtaining a shape of a blood vessel of the object and a thickness information using the intensity information;

obtaining a shape of the object using the intensity information;

performing modelling of a basic shape of the object by comparing the obtained shape of object with a pre-set shape;

determining the second shape of the blood vessel by combining the basic shape of the object and the first shape of the blood vessel; and obtaining a 3D information of the blood vessel using the second shape of the blood vessel, the thickness information, and the distance information, wherein the second shape is a shape reflected by a posture difference information of the first shape.

* * * * *